United States Patent [19]

Evans et al.

[11] Patent Number: 5,377,687

[45] Date of Patent: Jan. 3, 1995

[54] METHOD AND APPARATUS FOR PERFORMING MAPPING-TYPE ANALYSIS INCLUDING USE OF LIMITED ELECTRODE SETS

[75] Inventors: Arnold K. Evans; Mahesh H. Merchant, both of Kent, Wash.

[73] Assignee: Physio-Control Corporation, Redmond, Wash.

[21] Appl. No.: 196,019

[22] Filed: Feb. 14, 1994

Related U.S. Application Data

[63] Continuation of Ser. No. 944,398, Oct. 13, 1992, Pat. No. 5,318,037, which is a continuation of Ser. No. 697,332, May 9, 1991, Pat. No. 5,161,539.

[51] Int. Cl.$^6$ ............................................. A61B 5/452
[52] U.S. Cl. ..................................................... 128/700
[58] Field of Search ............... 128/695, 696, 700–706; 364/413.06

[56] References Cited

U.S. PATENT DOCUMENTS

| | | | |
|---|---|---|---|
| 4,023,564 | 5/1977 | Valiquette et al. | 128/2.06 |
| 4,106,495 | 8/1978 | Kennedy | 128/2.06 |
| 4,124,894 | 11/1978 | Vick et al. | 364/417 |
| 4,216,780 | 8/1980 | Rubel et al. | 128/699 |
| 4,318,412 | 3/1982 | Stanly et al. | 128/696 |
| 4,341,225 | 7/1982 | Gallant et al. | 128/710 |
| 4,517,983 | 5/1985 | Toyosu et al. | 128/639 |
| 4,530,365 | 7/1985 | Harada et al. | 128/696 |
| 4,680,708 | 7/1987 | Ambos et al. | 364/417 |
| 4,846,190 | 7/1989 | John | 128/731 |
| 4,850,370 | 7/1989 | Dower | 128/699 |
| 4,913,160 | 4/1990 | John | 128/731 |
| 4,924,875 | 5/1990 | Chamoun | 128/696 |
| 5,054,496 | 10/1991 | Wen et al. | 128/696 |
| 5,135,004 | 8/1992 | Adams et al. | 128/696 |

OTHER PUBLICATIONS

Abildskov et al., "The Present Status of Body Surface Potential Mapping," *JACC*, vol. 2, No. 2, pp. 394–396 (Aug. 1983).

Afifi et al., *Computer–Aided Multivariate Analysis*, II and III, Van Nostrand Reinhold Co.

Chen, *Statistical Pattern Recognition*, Hayden Book Co., 1973, pp. 36–38, 161.

Edwards et al., "Body Surface Potential Mapping to Monitor the Effects of Thrombolytic Therapy Following Acute Myocardial Infarction," *Journal of Electrocardiology*, vol. 22S, pp. 82–90.

Farr, et al., "Localization of Significant Coronary Arterial Narrowings Using Body Surface Potential Mapping During Exercise Stress Testing," *American Journal of Cardiology*, vol. 59, pp. 528–530 (Mar. 1987).

Fukunaga et al. "Application of the Karhunen-Loeve Expansion to Feature Selection and Ordering," *IEEE Transactions on Computers*, vol. C19, pp. 311–318 (Apr. 1970).

Han et al., "Nonuniform Recovery of Excitability in Ventricular Muscle," *Circulation Research*, vol. 14, pp. 44–60 (Jan. 1964).

Hirai et al., "Effects of Coronary Occlusion on Cardiac and Body Surface PQRST Isoarea Maps of Dogs with Adnormal Activation Simulating Left Bundle Branch Block," *Circulation*, vol. 77, No. 6, pp. 1414–1423 (Jun. 1988).

(List continued on next page.)

*Primary Examiner*—George Manuel
*Attorney, Agent, or Firm*—Christensen, O'Connor, Johnson & Kindness

[57] ABSTRACT

A system (10) is disclosed that includes a monitor (16) for use in performing 12-lead electrocardiographic (ECG) and body surface mapping (BSM) analyses on a patient (12) with a single ten-electrode cable set (14). The monitor receives nine leads of data from the electrode cable set and initially preprocesses it to simplify further analysis. Then the data is transformed to produce a spatial distribution relative to the patient's chest, representative of the data that would be collectible with a 192-electrode set. Feature extraction techniques are also described for use in evaluating transformed, as well as conventional, BSM data with respect to clinically evaluated populations. In that regard, features of interest are extracted from the data and statistically analyzed to detect select cardiac conditions.

24 Claims, 6 Drawing Sheets

OTHER PUBLICATIONS

Horan et al., "A Basis for Determining Body Surface Potential Patterns Attributable to Single-site Coronary Arterial Occlusion," *Journal of Electrocardiology*, vol. 22S, pp. 99–106.

Ko et al., "Data Acquisition System for Body Surface Potential Mapping," *Journal of Biioengineering*, vol. 2, No. 1-2, pp. 33–46 (Apr. 1978).

Kornreich et al., "Effective Extraction of Diagnostic ECG Waveform Informtaion Using Orthonormal Basis Functions Derived From Body Surface Potential Maps," *Journal of Electrocardiology*, vol. 18, No. 4, pp. 341 350 (1985).

Kornreich et al., "Multigroup Diagnosis of Body Surface Potential Maps," *Journal of Electrocardiology*, vol. 22S, pp. 169–178.

Kubota et al., "Relation of Cardiac Surface QRST Distributions to Ventricular Fibrillation Threshold in Dogs," *Circulation*, vol. 78, No. 1, pp. 171–177 (Jul. 1988).

Lux, "Electrocardiographic Body Surface Potential Mapping," *CRC Crit. Rev. Biomed. Eng.*, vol. 8, Issue 3, pp. 253–279 (1982).

Lux et al., "Clinically Practical Lead Systems for Improved Electrocardiography: Comparison with Precordial Grids and Conventional Lead Systems," *Circulation*, vol. 59, No. 2, pp. 356–363, (Feb. 1979).

Lux et al., "Limited Lead Selection for Estimation of Body Surface Potential Maps in Electrocardiography," *IEEE Transactions on Biomedical Engineering*, vol. 25, No. 3, pp. 270–276 (May 1978).

Lux et al., "Redundancy Reduction for Improved Display and Analysis of Body Surface Potential Maps, I. Spatial Compression," *Circulation Research*, vol. 49, pp. 186–196 (Jul. 1981).

Lux et al., "Statistical Representation and Classification of Electrocardiographic Body Surface Potential Maps", *IEEE Computers in Cardiology*, vol. 84, pp. 251–254, (1984).

Merchant et al., "Statistical Representation and Classification of Electrocardiographic Body Surface Potential Mapping", *American Heart Scientific Sessions*, (1980).

Scherer et al., "Synthesis of the 12-lead Electrocardiogram From a 3-lead Subset Using Patient-specific Transformation Vectors: An Algorithmic Approach to Computerized Signal Synthesis," *Journal of Electrocardiology*, vol. 22S, p. 128.

Schluter et al., "A Bedside Cardiac Arrhythmia Monitor," Eighth Annual Northeast Bioengineering Conference, pp. 381–385 (Mar. 1980).

Spekhorst et al., "Body Surface Mapping During Percutaneous Transluminal Coronary Angioplasty (PTCA): QRS Changes Indicating Regional Conduction Delay," *Circulation*, vol. 81, No. 3, pp. 840–849 (Mar. 1990).

Sridharan et al., "Use of Body Surface Maps to Identify Vessel Site of Coronary Occlusion," *Journal of Electrocardiology*, vol. 22S, pp. 72–81.

Szlavik et al., "An Interactive Small Computer System for ECG Analysis," *Proceedings of an International Symposium*, pp. 129–136 (Mar. 1977).

Thomas et al., "A Cardiac Potential Mapping System," *Journal of Electrocardiology*, vol. 22S, pp. 64–71.

Vincent et al., "Use of QRST Area Distribution to Predict Vulnerability to Cardiac Death Following Myocardial Inarction," *Circulation*, vol. 68, p. 352 (Oct. 1983), Abstract only.

Vondenbusch et al., "ECG-Mapping During Intracoronary Thrombolysis and Angioplasty," *IEEE Computers in Cardiology*, Oct. 1987, pp. 371–374.

METHOD AND APPARATUS FOR PERFORMING MAPPING-TYPE ANALYSIS INCLUDING USE OF LIMITED ELECTRODE SETS

This is a continuation of the prior application Ser. No. 07/944,398, filed Oct. 13, 1992, now U.S. Pat. No. 5,318,037, which in turn is a continuation of application Ser. No. 07/697,332, filed on May 9, 1991 and now issued as U.S. Pat. No. 5,161,539, the benefit of the filing dates of which are hereby claimed under 35 U.S.C. §120.

FIELD OF THE INVENTION

This invention relates generally to monitoring and analysis of the electrical activity of, for example, a patient's heart and, more particularly, to such monitoring and analysis of the spatial distribution of the electrical activity, based upon, for example, information collected from a limited number of electrodes.

BACKGROUND OF THE INVENTION

Many physiological activities have electrical signals associated therewith. For example, the operation of the heart is regulated by electrical signals produced by the heart's sinoatrial (SA) node. Normally, the SA node produces an electrical impulse roughly 60 times a minute.

Each impulse generated by the SA node initially spreads across the atria of the heart. After reaching the atrioventricular (AV) node of the heart, the impulse then travels downward to the ventricles. The electrical impulse depolarizes the muscle fibers as it spreads, with atrial and ventricular contractions occurring after the impulses pass. After contracting, the muscle cells are unable to react again for a short interval of time known as the refractory period. Eventually, the muscle fibers repolarize and return to their resting state.

As will be appreciated, the electrical activity initiated by the SA node is, thus, representative of the operation of a patient's heart. To allow the heart's operation to be analyzed, a variety of techniques have been developed for collecting and interpreting data concerning the electrical activity of the heart. Perhaps the most basic of these approaches is the three-lead electrocardiogram (ECG).

A three-lead ECG system typically employs a monitor and four "limb" electrodes, attached to the patient, to collectively monitor three voltages or "leads." Specifically, a left arm electrode (L) is placed on the patient's left arm. Similarly, a right arm electrode (R) is placed on the patient's right arm. A left leg electrode (F) is attached to the patient's left leg and a right leg or "ground" electrode (G) is attached to the patient's right leg.

As an electrical impulse spreads across the heart, the monitor repetitively measures the voltages at electrodes L, R, and F, relative to the ground electrode G. These voltages are designated vL, vR, and vF, respectively.

The first of the leads (I) evaluated by the monitor is equal to the difference between the voltages at electrodes L and R (I=vL-vR). Similarly, the second lead (II) monitored with the electrodes is equal to the difference between the voltages at electrodes F and R (II=vF-vR). Finally, the third lead (III) evaluated by the monitor is equal to the difference between the voltages at electrodes F and L (III=vF-vL).

The waveforms produced by plotting each of the leads over an interval of time corresponding to one cardiac cycle are conventionally divided into a number of segments. The portion of each waveform representing atrial depolarization is referred to as the "P" segment or wave. Depolarization of the ventricular muscle fibers is then represented by "Q," "R," and "S" segments of the waveform. Finally, the portion of the waveform representing repolarization of the ventricular muscle fibers is known as the "T" segment or wave.

To simplify the analysis of the three leads I, II, and III of data, the heart is generally treated as a dipolar source of electrical activity, positioned at the intersection of transverse, superior, and inferior axes of the patient's body. Each of the three leads is regarded as being equally sensitive to all sections of the heart. Lead I is, however, interpreted as representing electrical activity on the transverse axis, while leads II and III are interpreted as representing activity on the superior and inferior axes.

As will be appreciated, the leads are influenced by a variety of factors. For example, the size of the patient's heart, as well as its location and orientation relative to the patient's trunk, will affect the magnitudes of the leads. The presence of heart disease will also typically impact the waveforms. Further, the size, fat content, and air content of the patient's trunk, as well as the existence of any physical deformities or diseases, may influence the waveforms. Finally, the relative positioning of the electrodes on the patient may alter the waveforms sensed.

To properly interpret the three leads I, II, and III of data, a physician must be trained to recognize and identify the influence of these various factors. The physician must also understand the dipolar cardiac model and the resultant relationship between the three leads and the cardiac activity of interest.

In that regard, a physician's analysis of three-lead ECG data typically begins with the selection of the particular lead or leads to be reviewed. In that regard, because lead I reflects cardiac activity on the transverse body axis, the physician would most likely review lead I to detect lateral infarction or coronary vessel involvement. Similarly, because leads II and III reflect cardiac activity on the superior-inferior axes of the patient's body, they are reviewed to detect, for example, inferior disease.

Having selected a lead for analysis, the physician typically makes an initial assessment based upon the overall appearance of the waveform. The physician must also recognize the significance of particular features of the waveform. In that regard, a number of waveform features have been identified for use in diagnosing various heart conditions.

The area of the "QRST" segment of the waveform has been recognized as indicating disparity of recovery properties. As will be appreciated, the waveform's area can be computed by integrating the waveform over the interval of time during which the ventricular muscle fibers are depolarized and repolarized. A change in QRST area may indicate the presence of disease.

Another waveform feature used to diagnose the heart's condition is an analysis of the "ST" segment of the waveform. In that regard, the displacement of the ST segment is generally indicative of acute injury. For example, an elevated ST segment associated with Q waves indicates an acute or recent infarct. The analysis of the ST segment is usually based upon data collected from more than the three leads describes above.

A related form of analysis is referred to as "late-potential" analysis. Late-potential analysis involves the expansion of the time-scale of the QRS segment of the waveform and a detailed review of the expanded segment for features not apparent in a conventional display of the waveform. More particularly, the expanded segment is reviewed for low level activity that persists into the ST segment.

While the three-lead system described above is generally useful in evaluating the condition of the patient's heart, it does have certain limitations. For example, because the three-lead analysis is based upon a dipolar view of the heart, the leads have little selective sensitivity to the operation of particular regions of the heart. Depending upon the nature of the cardiac event to be detected, this lack of sensitivity may prevent the three-lead data from being diagnostically useful.

One effort to increase the regional sensitivity of ECGs led to the development of "12-lead" ECGs. A 12-lead ECG system includes the limb electrodes of a conventional three-lead ECG system. In addition, a 12-lead system includes six "precordial" electrodes, positioned on the patient's chest. The six precordial electrodes were originally added to allow the electrical activity of individual regions of the heart to be more directly sensed. In practice, however, the dipolar model of the heart has been retained and the 12 leads interpreted to evaluate electrical activity along the three axes.

Although the 12-lead ECG configuration has been described as allowing a limited form of "mapping" to be performed, for the purposes of the ensuing discussion it will be more precisely referred to as a technique for introducing selective sensitivity into the leads of an ECG system. In contrast, as will be described in greater detail below, mapping is more appropriately used to describe approaches involving the evaluation or presentation of spatial distributions of data over the patient's chest.

Reviewing the construction and operation of a 12-lead ECG system in greater detail, as noted above, six precordial electrodes are added to the four limb electrodes of a three-lead ECG system. In that regard, a first precordial electrode (p1) is attached to the front of the patient's chest, to the right of the sternum in the fourth rib interspace. A second precordial electrode (p2) is also attached to the front of the patient's chest, left of the fourth rib interspace. A fourth precordial electrode (p4) is positioned at the left midclavicular line in the fifth rib interspace. The third precordial electrode (p3) is positioned midway between electrodes p2 and p4. Finally, the fifth precordial electrode (p5) is positioned at the midaxillary line in the fifth rib interspace and the sixth precordial electrode (p6) is positioned midway between electrodes p4 and p5.

The 12-leads or waveforms evaluated with the four limb electrodes and six precordial electrodes are as follows. In addition to the three leads I, II, and III already described, three leads aVR, aVL, and aVF are formed from the voltages sensed at the limb electrodes. In that regard, lead $aVR = vR - (vL + vF)/2$; lead $aVL = vL - (vR + vF)/2$; and lead a $VF = vF - (vL + vR)/2$.

The six precordial electrodes p1, p2, p3, p4, p5, and p6 are used to sense voltages v1, v2, v3, v4, v5, and v6, respectively, referenced to the ground electrode G. The remaining six leads are designated V1, V2, V3, V4, V5, and V6. In that regard, lead $V1 = v1 - (vR + vL + vF)/3$; lead $V2 = v2 - (vR + vL + vF)/3$; lead $V3 = v3 - (vR + vL + vF)/3$; lead $V4 = v4 - (vR + vL + vF)/3$; lead $V5 = v5 - (vR + vL + vF)/3$; and lead $V6 = v6 - (vR + vL + vF)/3$.

As will be appreciated, the 12 waveforms produced by such a system each have the various PQRST segments described above. In analyzing the 12-lead data, the physician may consider the overall appearance of the waveforms, as well as the various waveform features discussed above in connection with the three-lead system. In addition, because the 12-lead ECG contains considerably more information that the conventional three-lead ECG, the physician may choose to review only a few of the numerous leads, with the particular leads selected depending upon the cardiac features of interest.

In that regard, the dipolar model of the heart is almost universally relied upon in the analysis of 12-lead ECGs. Leads I, aVL, aVR, V5, and V6 reflect cardiac activity on the transverse body axis and are monitored to evaluate lateral disease. Leads II, III, and vF are indicative of electrical activity on the superior-inferior axes and are reviewed to evaluate inferior disease. Finally, leads V1, V2, V3, and V4 represent activity on the anteroposterior axis and are monitored to determine anterior and posterior disease.

One alternative use of the conventional 12-lead ECG system described above is the performance of a stress test. The system is virtually the same with the exception that electrodes L and R are moved from the patient's arms to the trunk. As a result, leads I, II, III, aVR, aVL, and aVF are attenuated. Cardiac stress is introduced by subjecting the patient to a regimen of vigorous exercise and the resultant leads are analyzed in conventional fashion.

As noted previously, although the 12-lead ECG originally represented an effort to adopt a regionally differentiated model of cardiac activity in place of the dipolar model, both the three-lead and 12-lead ECG are conventionally analyzed as representing the activity of a dipolar cardiac generator. Serious efforts to provide selective sensitivity to the operation of particular regions of the heart were initiated by the introduction of body surface mapping (BSM) systems. Such systems evaluate or present spatial distributions of data over the patient's chest.

Conventional body surface mapping systems employ a relatively large number of electrodes in comparison to the three-lead and 12-lead ECG systems described above. For example, much of the work done in the area of body surface mapping has been with systems employing 192 electrodes. As will be appreciated, the use of such a large number of electrodes allows the spatial distribution of voltage across the patient's chest to be relatively closely evaluated.

Unlike the ECGs discussed above, in which each lead is displayed as a time-dependent waveform, the voltages sensed at the BSM electrodes are often plotted as part of a map of the patient's chest. More particularly, the two-dimensional layout of the electrodes relative to the patient is first plotted. Then, for each point in the cardiac cycle at which measurements are made, the electrode sites having the same voltages are connected by contour lines, commonly referred to as "isopotential"

lines. As a result, a series of isopotential maps are generated for for each cardiac cycle.

Although the generation of isopotential maps is relatively easy to accomplish, their interpretation can be difficult. In that regard, some relationship between the contours of the isopotential map and the particular cardiac features of interest must be established. Although a physician can make an initial evaluation based upon visual comparisons with referential maps generated for populations of known physiology, the volume of data contained in the series of maps generated over one cardiac cycle can be overwhelming. Further, because mapping is not presently widely performed, the physician's experience and familiarity with referential maps may be somewhat limited.

A variety of techniques have been developed to reduce the complexity of map analysis. For example, one way of reducing the volume of data to be dealt with involves integration of the voltages sensed at each of the electrodes over an interval of time. In that regard, if the voltage at a given electrode is plotted as a function of time, the resultant waveform generally includes the P, Q, R, S, and T segments described above. By integrating that voltage over, for example, the QRS or ST interval, a single value indicative of the sensed voltage at the electrode is produced.

A single isointegral map, representative of cardiac activity over an entire cycle, can then be generated as follows. As with the isopotential map, the two-dimensional arrangement of the electrodes relative to the patient's chest is first plotted. Next, the integrals of the waveforms at the various electrode sites are evaluated and those electrode sites having the same integral values associated therewith are connected by lines, commonly referred to as "isointegral" contours. As a result, a single isointegral map is produced representing cardiac activity over one cycle.

Even with the data reduced to a single map per cardiac cycle, interpretation can be somewhat difficult. Each map includes a multitude of potentially significant contours to be evaluated by the physician. The experience required to meaningfully interpret these contours based solely upon a visual review is considerably more extensive than that required to evaluate 12-lead ECGs. Such evaluation is further hampered by the relatively limited information available correlating map contours with cardiac activity.

To enhance the value of such maps, increasing efforts are being made to identify significant map features and to develop systems that automatically extract such features from map data. With the appropriate features extracted, a physician can then more quickly and easily interpret the data.

In that regard, one approach to feature extraction that is of particular interest is described in an article by Lux et al., entitled "Redundancy Reduction for Improved Display and Analysis of Body Surface Potential Maps, I. Spatial Compression," appearing in Volume 49 of Circulation Research at pages 186–196. Lux et al. disclose an approach in which a Karhunen-Loeve transform is used to compress the data to produce a basis function vector that allows the data to be reconstructed with minimum representational error. A stepwise discriminant analysis is then applied to the vector coefficients to classify the patient as diseased or normal. While the Lux et al. approach is a useful tool in the evaluation of BSM data, as will be described in greater detail below, the disclosed technique fails to consider the potential influence of noncardiac patient variables on the analysis and does not adequately address the extraction of particular features of interest from the data.

In addition to reducing the complexity of BSM data analysis, attempts have been made to reduce the complexity of the data collection process. As will be appreciated, with 192 electrodes required to successfully generate a surface distribution of electrical activity, the time required to prepare a patient for data collection is significant. The electrode set required is further unwieldy, expensive, and may contribute to patient apprehension. Each of these factors tends to limit the utility of BSM data analysis.

One work that is of particular interest in the area of "limited-lead" mapping is the article by Lux et al., entitled "Clinically Practical Lead Systems for Improved Electrocardiography: Comparison with Precordial Grids and Conventional Lead Systems," appearing in Volume 59 of Circulation at pages 356–363. In this article, Lux et al. investigate the utility of several different lead sets in replicating the data collected with "conventional" 192 electrode BSM systems. More particularly, sets of 32, 30, and 9 leads are evaluated. Data collected from the limited leads is then transformed to represent data collected from a conventional lead set. Based upon the evaluation of this transformed data, Lux et al. conclude that 20–35 electrodes are required for BSM analyses.

More particularly, Lux et al. emphasize numerous shortcomings of the nine lead data transformation. For example, Lux et al. note that the pattern error and root-mean-square (rms) error for the nine-lead set is larger than the errors occurring when 32-lead arrays are used. Lux et al. conclude that the nine-lead array misses electrocardiographic information and that 20–35 electrodes are required for mapping.

Efforts have also been devoted to the use of BSM data to identify particular cardiac anomalies of interest. For example, the subject of coronary artery narrowing is addressed in an article by Farr et al., entitled "Localization of Significant Coronary Arterial Narrowings Using Body Surface Potential Mapping During Exercise Stress Testing," appearing in Volume 59 of the American Journal of Cardiology at pages 528–530, and an article by Sridharan et al., entitled "Use of Body Surface Maps to Identify Vessel Site of Coronary Occlusion," appearing in Volume 22S of the Journal of Electrocardiology at pages 72–81. As will be described in greater detail below, however, these approaches are limited by the form of the data analyzed, the feature extraction techniques used, and their ability to quantify, as well as localize, arterial narrowings.

Another specific anomaly of interest is the heart's "inducibility", or susceptibilty to externally induced arrhythmia. The subject of inducibility is addressed to some extent, for example, in an article by Vincent et al. entitled "Use of QRST Area Distribution to Predict Vulnerability to Cardiac Death Following Myocardial Infarction", appearing in Volume 68 of Circulation at page 352, an article by Kubota et al. entitled "Relation of Cardiac Surface QRST Distribution to Ventricular Fibrillation Thresholds in Dogs", appearing in Volume 78 of Circulation at pages 171–177, and an article by Han et al., entitled "Nonuniform Recovery of Excitability in Ventricular Muscle", appearing in Volume 14 of Circulation at pages 44–60. Again, however, the disclosed approaches are somewhat limited in nature and applicability.

As will be appreciated from the preceding discussion, it would be desirable to provide a system that would allow a spatial distribution representative of, for example, the electrical activity of a heart to be analyzed without requiring the use of complex electrode configurations for data collection. The system should, however, take advantage of the added information content present in the spatial distribution. In addition, the system should format the spatially distributed data in a manner suitable for the particular feature to be extracted. The system should further be able to extract the features in a manner that distinguishes noncardiac influences on the data and that offers increased analytical capabilities with respect to particular features of interest.

SUMMARY OF THE INVENTION

In accordance with one aspect of the invention, a system is disclosed for monitoring a first set of electrical signals received from a patient at less than 20 electrodes and analyzing that first set of electrical signals to obtain information that is conventionally available from a second set of electrical signals collected from a greater number of electrodes. The system includes a transformation subsystem for receiving the first set of electrical signals and for transforming the first set of electrical signals into a map-type data set representative of the second set of electrical signals. An extraction subsystem is also included for extracting at least one feature from the map-type data set.

In accordance with another aspect of the invention, a method is disclosed for monitoring and analyzing a first set of electrical signals, received from a patient at less than 20 electrodes and conventionally analyzed on the basis of the signals' temporal chacteristics. The method includes the step of transforming the first set of electrical signals into a transformed data set including information regarding the spatial distribution of the electrical signals relative to the patient. The method also includes the step of processing the transformed data set to evaluate at least one patient feature of interest.

In accordance with yet another aspect of this invention, a method is disclosed for processing information that is spatially representative of the electrical activity of a patient's heart to detect the presence of at least one cardiac characteristic of interest. The method includes the step of producing a data set that is usable in representing the information representative of the electrical activity of the patient's heart. A data subset is then identified from the data set for use in detecting the cardiac characteristics of interest. Finally, a feature value is computed from the subset for use in detecting the presence of the characteristics.

In accordance with still further aspects of the invention a method is disclosed for reducing the influence of noncardiac parameters on data representing the spatial distribution of electrical activity across a patient's chest. Another method is disclosed for evaluating the magnitude of a cardiac characteristic of interest. Additional methods are disclosed for detecting the presence of coronary artery stenosis in a patient, as well as the patient's susceptibility to externally induced arrhythmias.

BRIEF DESCRIPTION OF THE DRAWINGS

The invention will presently be described in greater detail, by way of example, with reference to the accompanying drawings, wherein.

DETAILED DESCRIPTION OF THE PREFERRED EMBODIMENT

Figure 1:
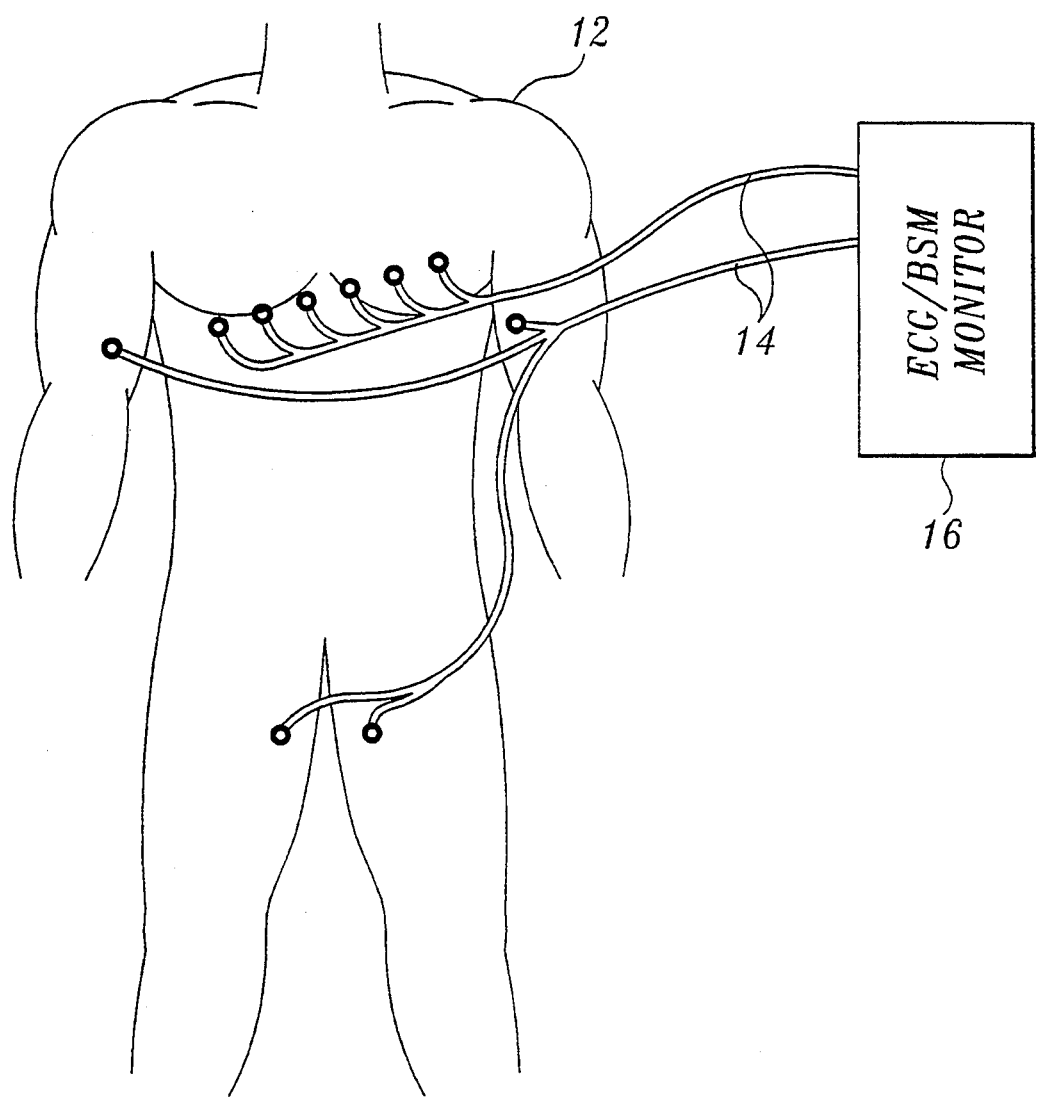
FIG. 1 illustrates a 12-lead ECG/BSM system, constructed in accordance with this invention, attached to a patient.

A 12-lead ECG/BSM system 10, constructed in accordance with this invention, is shown attached to a patient 12 in FIG. 1. The system 10 can be used to perform traditional 12-lead ECG analyses of the patient's heart. In addition, system 10 can be used to collect and analyze information regarding the spatial distribution of the heart's electrical activity.

As will be described in greater detail below, the spatial analysis or body surface mapping performed by system 10 is accomplished with significantly fewer electrodes than was previously deemed possible. As a result, system 10 is simpler than conventional BSM systems. Because system 10 can be attached to patient 12 more quickly and easily than conventional BSM systems, its clinical value is also enhanced.

The manner in which the spatial data is processed by system 10 similarly offers several advantages over the feature extraction techniques conventionally employed. For example, by employing QRST integral information, the performance of a preferred arrangement of system 10 is not dependent upon the activation sequence exhibited by the patient's heart. Further, the system 10 may normalize the mapped data prior to feature extraction to eliminate the effect of a variety of noncardiac patient variables on the analysis. An additional enhancement involves the system's ability to detect, distinguish, and quantify local cardiac anomalies. Yet another feature of the system 10 involves a technique that may be employed to reduce the complexity of the representations of the mapped data required for further analysis.

Figure 2:
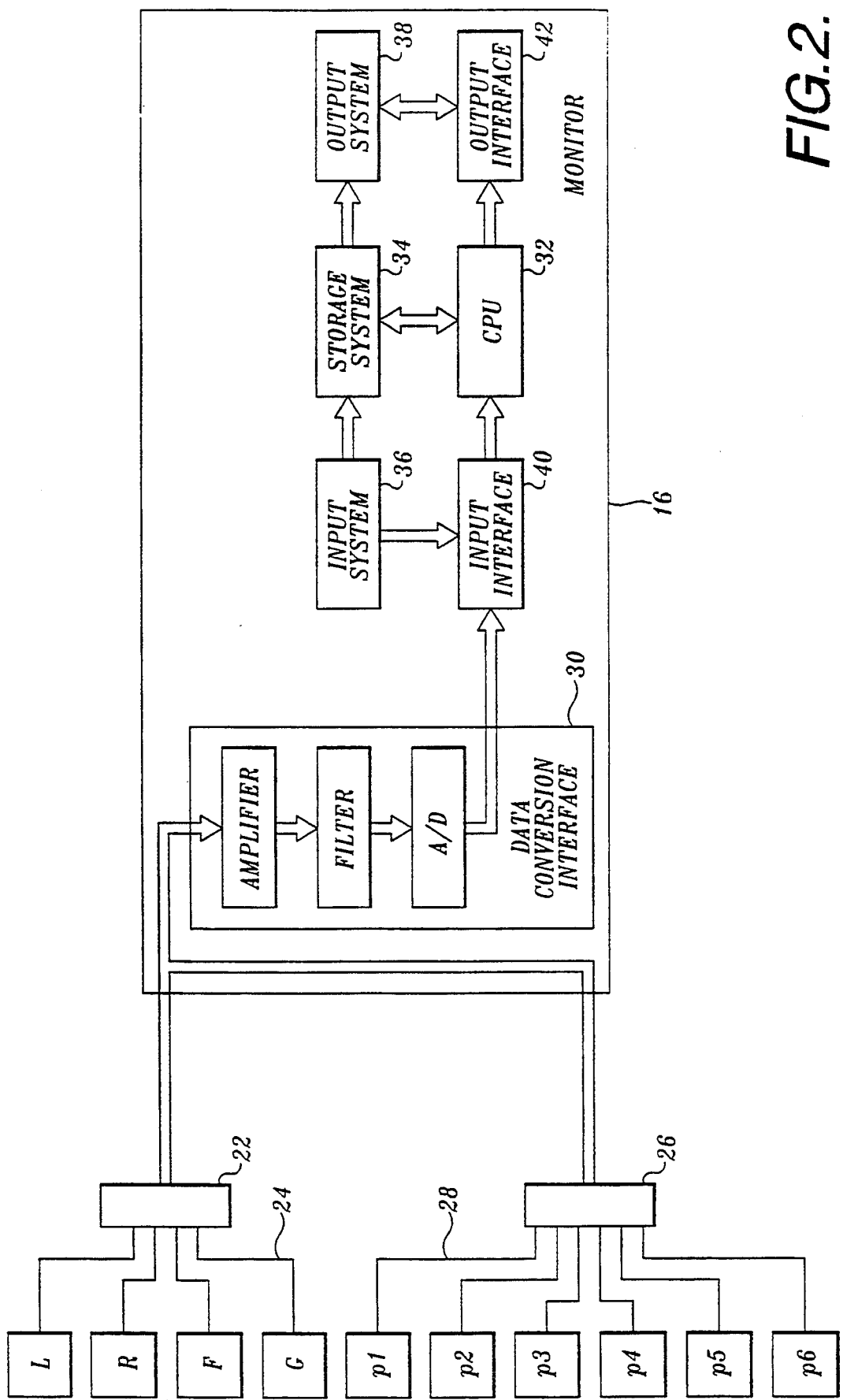
FIG. 2 is a block diagram of the ECG/BSM system of FIG. 1.

Reviewing the construction of system 10 in greater detail, reference is had to the block diagram of FIG. 2. As shown, the ECG/BSM system 10 broadly includes an electrode cable set 14 and an ECG/BSM monitor 16. The electrode cable set 14 is attached to patient 12 and electrically connects the patient 12 to monitor 16. The monitor 16, in turn, senses the electrical activity of the patient's heart through the electrode cable set 14 and produces outputs that are used by a physician in making ECG-based and BSM-based diagnoses.

The electrode cable set 14 is conventional in design and includes a four-electrode limb set 18 and a six-electrode precordial set 20. Addressing these components individually, the limb set 18 includes limb electrodes L, R, F, and G, which are electrically connected to a limb set connector 22 by a four-conductor cable set 24. Electrodes L, R, F, and G are preferably designed to provide a low-impedance, adhesively maintained interface with patient 12. The connector 22 and cable set 24 provide electrically independent, conductive paths for the cardiac signals sensed at the four electrodes L, R, F, and G.

The precordial set 20 includes six precordial electrodes p1, p2, p3, p4, p5, and p6. These six electrodes are connected to a common precordial set connector 26 by a six-conductor cable set 28. The electrodes p1, p2, p3, p4, p5, and p6 are also designed to provide a low-impedance, adhesively maintained interface with patient 12. The connector 26 and cable set 28 provide electrically independent, conductive paths for the cardiac signals sensed at the six precordial electrodes. As will be appreciated, it may be desirable to modify the number and location of electrodes used.

Addressing now the construction of the monitor 16 in greater detail, as shown in FIG. 2, monitor 16 includes a data conversion interface 30, central processing unit (CPU) 32 (such as an Intel 386 CPU), data storage system 34, input system 36, output system 38, input interface 40 and output interface 42. Preferably, these components are housed in a single unit. As will be appreciated, however, the monitor 16 may be a system of discrete components including a personal computer, with supporting peripherals and interfaces.

Addressing these various components individually, the data conversion interface 30 preferably includes a number of elements. For example, interface 30 may include an amplifier circuit 44, which amplifies the relatively low-level cardiac signals received from cable set 14 to a level that is sufficient for subsequent processing. If desired, a filter circuit 46 having a bandwidth of 0.1 to 250 Hertz, may also be included to remove noise from the received signals. Finally, an analog-to-digital (A/D) converter 48 is included to convert the analog cardiac signals into a digital form of suitable resolution for analysis by the CPU 32. The interface 30 preferably includes nine channels to allow nine leads of data to be received and processed simultaneously.

The central processing unit (CPU) 32 is included to process the cardiac signals received from interface 30. As will be described in greater detail below, the CPU 32 processes these signals with the aid of stored data and instructions, as well as various operator-generated inputs. The CPU 32 processes this information to generate displays used by the physician in 12-lead ECG and BSM diagnosis. The data storage system 34 has a variety of responsibilities. In that regard, system 34 retains the various program instructions that govern the manner in which CPU 32 processes the received cardiac signals. In addition, system 34 stores information about the cardiac signals in various formats as the signals are being processed. Finally, the storage system 34 stores referential data representing the cardiac activity of normal and diseased patients for use by CPU 32 in interpreting the cardiac signals received from the electrode cable set 14.

As will be appreciated, the data storage system 34 may include random-access memory (RAM) and read-only memory (ROM) in chip form. The storage capability may be supplemented by the addition of floppy or hard-disk storage systems. Such components of the data storage system 34 may be included within, or external to, the monitor 16.

The input system 36 is included to allow the operator to provide data and instructions to the monitor 16. In that regard, the input system 36 may include a control panel or keyboard for use in controlling the monitor 16. Such a control panel allows, for example, the monitor 16 to be turned ON and OFF, ECG or BSM modes of operation to be selected, a particular diagnostic approach to be chosen, or a particular display technique to be used. In addition, the input system 36 may be designed to allow program instructions to be written into storage system 34 through a keyboard or directly downloaded from a remote storage system.

The output system 38 includes a variety of devices useful to a physician in evaluating the performance of monitor 16 and the condition of the patient's heart. For example, the output system 38 may include displays that indicate whether the monitor 16 is ON and whether the ECG or BSM mode of operation has been selected. The output system 38 may further include a CRT or printer for displaying selected QRST waveforms used in ECG analyses, as well as isopotential and isointegral surface distributions used in BSM analyses. Finally, the output system 38 may include individual visible and audible displays indicative of particular cardiac conditions detected by the CPU 32, as described in greater detail below.

The input interface 40 connects the input system 36 to the CPU 32. As will be appreciated, interface 40 is designed to condition input signals so that they can be applied to, and properly interpreted by, CPU 32. The output interface 42, in turn, connects the output system 38 to CPU 32 and is designed to condition the outputs of CPU 32 so that they are usable by the output system 38.

Having reviewed the basic components of the ECG/BSM system 10, the operation of system 10 will now be considered in greater detail. In that regard, the electrode cable set 14 is attached to patient 12 in accordance with conventional 12-lead protocols. As previously described in detail, the limb electrodes L, R, F, and G are connected to the patient's limbs and the precordial electrodes p1, p2, p3, p4, p5, and p6 are connected to the patient's chest. The positioning of the electrodes influences the strength of the received signals and, thus, is important in ensuring the proper analysis of cardiac activity.

With the electrode cable set 14 properly attached to patient 12, the monitor 16 offers several different modes in which the patient's cardiac activity can be evaluated. For example, a physician can instruct the monitor 16 to operate in an ECG mode by appropriately actuating controls in the input system 36. In this ECG mode, the monitor 16 causes the output system 38 to selectively display the twelve leads of ECG data for analysis by the physician. The operation of system 10 in the ECG mode is conventional and need not be discussed in further detail here.

The operation of system 10 in a BSM mode is, however, of particular interest and is described in greater detail in connection with the flow chart shown in FIG. 3. In that regard, the physician first instructs the monitor 16 to operate in the BSM mode by actuating the appropriate control in the input system 36, as shown in block 50 of the flow chart. In the BSM mode, monitor 16 receives analog signals representative of the potentials at the L, R, F, p1, p2, p3, p4, p5, and p6 electrodes, measured relative to the potential of the ground electrode G.

These nine signals are initially applied to the data conversion interface 30 at block 52. As noted previously, the interface 30 is preferably a nine-channel system, allowing each of the signals to be continuously received and processed by the monitor 16. The amplifier circuit 44 amplifies the signals at block 54 and the filter circuit 46 removes undesirable frequency components therefrom at block 56. Finally, at block 58, the A/D converter 48 converts the analog signals into digital form.

Figure 3:
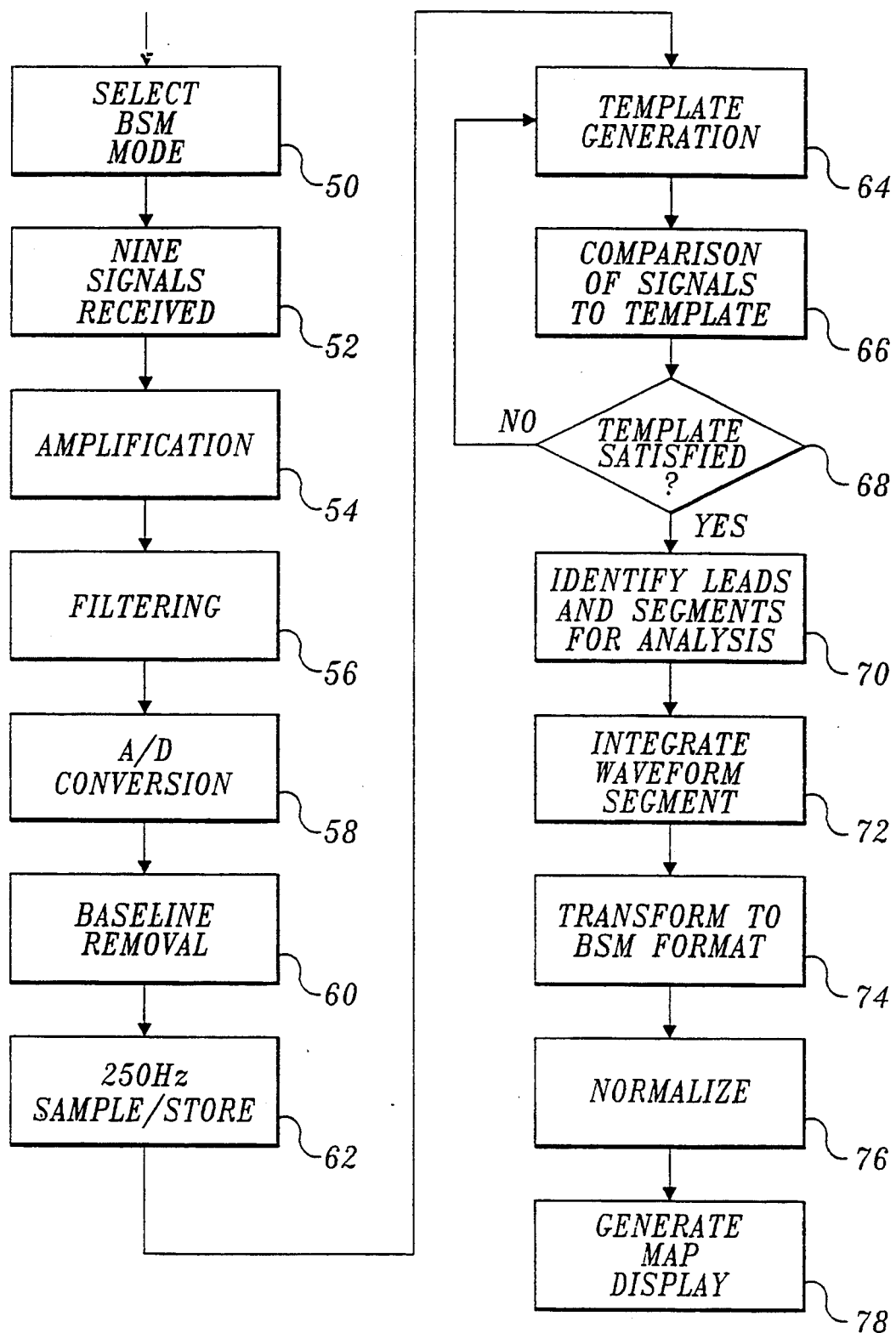
FIG. 3 is a flow chart illustrating the manner in which the system of FIG. 1 receives data from the patient and transforms it into a conventional BSM format.

From this point on, the operation of system 10 depicted in the flowchart of FIG. 3 represents steps performed by CPU 32 in response to program instructions stored in system 34. The first of these operations, shown in block 60 is the removal of offset components to establish a baseline from which signals can be more readily compared and analyzed. Next, at block 62, each of the nine signals are simultaneously sampled and stored in system 34, at the conventional 250 Hertz sample rate used by 12-lead ECG systems.

The next series of preprocessing steps performed by the CPU 32 is designed to identify when the received cardiac signals are suitable for further analysis. At block 64, the CPU 32 evaluates, for example, one of the nine signals over a single cardiac cycle. The CPU 32 generates a waveform template having certain amplitude and temporal characteristics that are indicative of the signal selected, during the cycle reviewed.

Then, at block 66, the CPU 32 compares the signal received over several consecutive cardiac cycles with the template. If the signal continues to exhibit a periodic waveform whose amplitude and temporal characteristics are within set tolerances of the template values, the signal is stable and is considered to be an accurate representation of cardiac activity. As a result, the CPU 32 will be directed to analyze all nine signals collected over the last cardiac cycle, at block 68.

On the other hand, if the template parameters are not satisfied by the signal over the consecutive cycles reviewed at block 66, the CPU 32 is directed to restore operation to block 64. As a result, a new set of template parameters will be generated at block 64. The signal will then be compared to the new template over several subsequent cardiac cycles at block 66. Eventually, the template parameters will be satisfied and the operation of CPU 32 will proceed to block 70.

Figure 4:
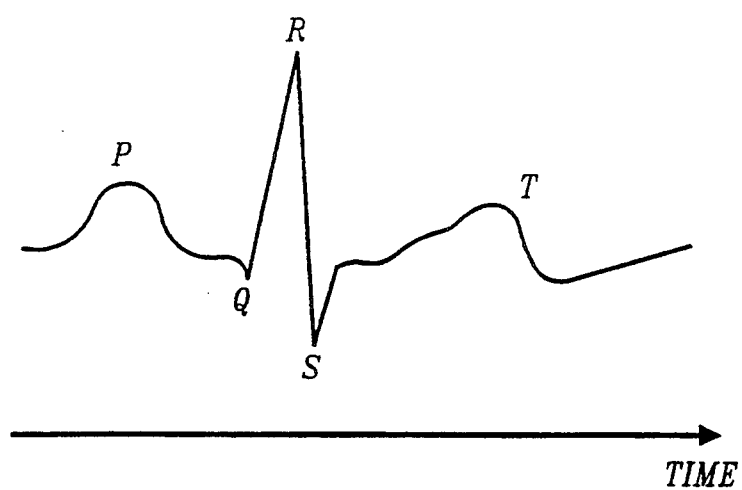
FIG. 4 is a graph of one lead of data, plotted as a function of time over one cardiac cycle.

At block 70, CPU 32 reviews the nine signals collected during the cardiac cycle selected by the template comparison process reviewed above. FIG. 4 is an illustration of one of the nine signals, for example, the potential at electrode p1 relative to electrode G, plotted over one cardiac cycle. As shown, the signal exhibits the conventional PQRST segments.

In further processing the nine signals, the CPU 32 first computes the twelve leads of data used in 12-lead ECG analysis. Thus, the conventional leads are readily available for display when the ECG/BSM system 10 is used in the ECG mode.

The CPU 32 also identifies the portion of the nine signals to be analyzed by system 10 in the BSM mode. Assuming first that the QRST portion of each signal is to be evaluated, the CPU 32 identifies the beginning of the Q segment and the end of the T segment of each signal. The identification of these points can be accomplished by monitoring the signals for slope reversals occurring at intervals in which such transitions are expected to occur. With the beginning of the Q segment and the end of the T segment established as end points, the CPU 32 then limits further analysis of the nine signals to those portions of the signals occurring between the end points.

As will be appreciated, the QRST intervals of the conventional twelve leads could be computed in place of the corresponding intervals of the nine electrode signals. Because the desired spatial information is contained directly in the nine signals, however, the complexity of subsequent processing is reduced by eliminating the twelve-lead conversion.

Once the QRST intervals of interest have been determined, the CPU 32 proceeds to integrate each of the nine intervals at block 72. As will be appreciated, nine numeric values, corresponding to the area under the nine QRST curves, are thus computed for the cardiac cycle being reviewed. As a result, the complexity of the information to be further processed is reduced by a factor of 250.

Another advantage of using the QRST area, as opposed to the waveform itself or some limited portion of the waveform, is that the QRST area is relatively independent of the activation sequence of the myocardial cells. Thus, an anomaly in myocardial conduction, such as, for example, a bundle brand blockage, that is unrelated to the cardiac feature of interest will not alter the QRST area computation or any further analysis based upon that computation.

At block 74, the CPU 32 is called upon to begin a transformation of the nine values computed at block 72 for use in preparing a body surface map. In that regard, the essence of this transformation is the conversion of data that is conventionally analyzed on a temporal basis into a format for use in a spatial analysis.

By way of illustration, assume that a 192-electrode set represents the conventional standard number of electrodes required to fully evaluate the spatial distribution of signals across the patient's chest. The pattern of these 192 electrodes is shown graphically in the map of FIG. 5 and includes 16 columns of 12 sites each.

Figure 5:
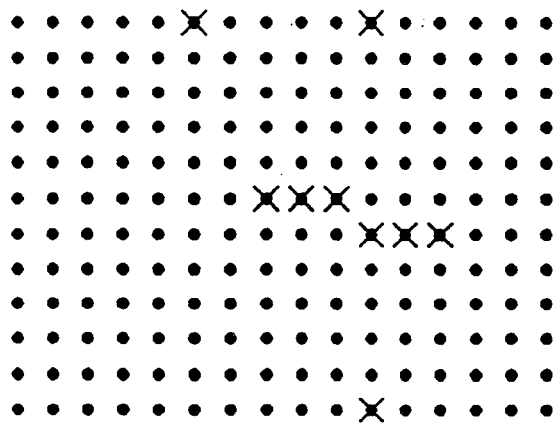
FIG. 5 is a graph of the location of ten electrodes employed in the ECG/BSM system of FIG. 2, relative to a conventional 192-electrode mapping system.

Of these 192 "standard" electrode sites, the nine sites whose physical location corresponds most closely to the location of properly placed conventional electrodes L, R, F, p1, p2, p3, p4, p5, are identified. In FIG. 5, these sites are identified with the letter x. With the appropriate limited-lead set identified, a linear transformation of data from the nine electrode sites to 192 electrode sites can be accomplished in the manner taught by Lux et al., cited above.

More particularly, at block 74 the CPU 32 computes a transformed vector A1, which includes the set of 192 transformed values, as follows: $A1 = E(A2) + (T1)(A3 - E(A3))/T2$; where E is a mathematical expectation operator; A2 is a vector including a referential 192 lead data set stored for use in performing the transformation; A3 is a vector including the nine values measured for the patient; T1 is the cross-covariance matrix of A2 and A3; and T2 is the covariance matrix of A3.

On a functional level, this process involves a linear transformation employing a 9-row, 183-column matrix retained in storage system 34. This transformation matrix is computed from data measured with a 192-electrode set and each point in the matrix is a least-squares approximation of the value required to ensure that the sum of the possible squared prediction errors, occurring when the transformation is performed, is kept to a minimum.

Once the transformed vector has been determined, CPU 32 preferably normalizes the vector to unit length at block 76. As will be appreciated, the magnitudes of the electrical signals received at the various electrodes are a function of a variety of factors. Some of these factors are related to the operation of the patient's heart and may be indicative of a particular anomaly of interest. On the other hand, other factors, including such volume-conductor related parameters as the patient's weight, age, and sex, may also influence the amplitude of the signals received. As a result, the signals received from two patient's with identical heart conditions may exhibit significantly different amplitudes.

The normalization step removes this form of noncardiac differentiation between patients. In that regard, each element of the 192 element vector is squared and their sums added, with the magnitude of the vector being equal to the square root of that quantity. By dividing each of the 192 elements by the vector magnitude, the vector is then normalized to have a magnitude of one. As a result, the patterns of the signals are retained but the potentially skewing influence of noncardiac patient parameters is eliminated. As will be appreciated, information regarding the magnitude of the signal can still be retained, if desired.

Figure 6:
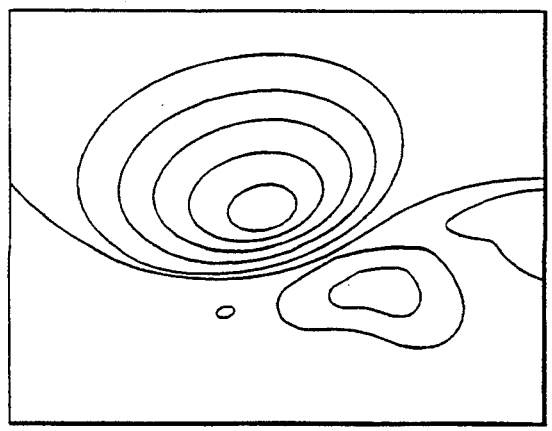
FIG. 6 illustrates an isointegral map generated by the ECG/BSM system.

Once the normalized, transformed vector has been determined, CPU 32 may instruct the output system 38 to display the vector as a series of isointegral lines at block 78. In that regard, the transformed vector includes 192 numbers that are representative of the QRST area that would have been expected to be measured if 192 electrodes had been employed in place of the nine relied upon. The output system 38 displays a map, shown in FIG. 6, representative of the 192 electrode sites and joins those sites having substantially the same number assigned thereto by lines. As a result, the map of the patient's chest includes a set of isointegral contour lines indicative of the integrals of the QRST areas that would be expected to be measured at points along the contour lines.

A physician who is experienced in reviewing the body surface maps of patients having known cardiac diseases can visually analyze the mapped transformation data to look for features potentially indicative of cardiac disease. As noted previously, however, the work by Lux et al. indicates that such analyses would not be useful because the correlation between data transformed from nine leads and data measured with 192 leads is not sufficiently high. However, despite the low correlation, applicants have discovered that nine-lead transformed data can be quite useful in detecting and analyzing certain cardiac anomalies.

The preceding discussion describes one approach to the collection of information concerning the spatial distribution of electrical activity across the patient's chest. By successfully using an electrode configuration that is conventionally used to provide only a temporal evaluation of the electrical activity, the physical and operational complexity of the spatial analysis is advantageously reduced. The following discussion of the extraction of features from the transformed BSM data applies equally well, however, to the analysis of data collected from conventional BSM electrode sets.

Figure 7:
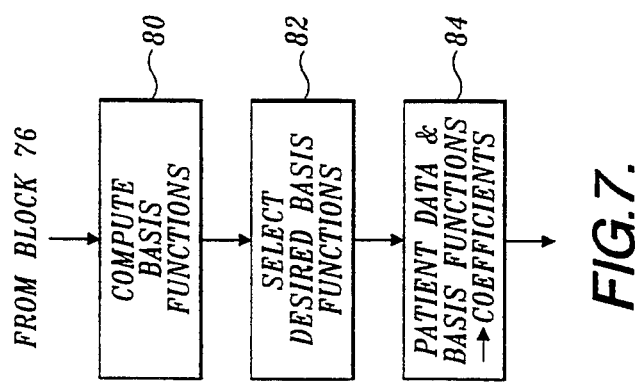
FIG. 7 is a flow chart illustrating one way in which the transformed BSM data produced in FIG. 3 is compressed for further analysis by the ECG/BSM system.

Addressing now the manner in which the analysis of the transformed BSM data by ECG/BSM system 10 proceeds, reference is had to FIG. 7. Although the physician can simply analyze the data based upon a visual review, the extent and subtleties of the information content in the map, along with the limited experience of most physicians in the review of BSM data, make it desirable for the CPU 32 to perform additional feature extraction and analyses.

To that end, the CPU 32 first attempts to further reduce the volume of information to a more manageable level. One such approach involves the representation of the mapped data by a set of basis functions, as indicated at block 80. These basis functions are essentially a set of building blocks that can be used to reconstruct the mapped data. The advantage of using the basis functions is that the functions, as well as the way in which they must be combined to reconstruct the data set, can be stored and evaluated more easily than the mapped data itself.

The most commonly used basis functions in nonmapping data compression applications are sinusoidal functions used to reconstruct data on the basis of its frequency content. However, in many instances, it is possible to identify nonsinusoidal basis functions that are more useful either because they are computationally more efficient or because they permit greater data compression.

In one embodiment, the CPU 32 identifies the most representative basis functions for subsequent analysis at block 80. In that regard, a Karhunen-Loeve (KL) expansion is used to identify those basis functions that allow the difference between the mapped data and a reconstruction achieved with the basis functions, i.e., the representation error, to be minimized. The basis functions selected are the eigenvectors of the covariance matrix of the data, ordered by decreasing eigenvalue magnitude. KL expansions are described in greater detail in, for example, Chen, Statistical Pattern Recognition, pages 36–38 and 161.

The KL expansion results in the production of 192 basis functions. In the preferred arrangement, however, only the twelve highest order functions are used at block 82. The original 192-dimension map M can then be expressed as:

$$\sum_{i=1}^{12} c_i(\phi_i)$$

where $\phi_i$ represents the basis functions selected and $c_i$ represents coefficients that can be used with the basis functions to reconstruct the map M.

These twelve basis functions are small enough in number to be manageable from a processing standpoint, while still preserving a sufficient amount of information to be useful in evaluating the particular cardiac anomaly or anomalies of interest. Although error theoretically decreases with the inclusion of additional basis functions, experience indicates that the response becomes relatively flat when more than ten functions are used and, for example, the use of 18 basis functions does not appear to provide any better results than 12 basis functions.

Although the use of the KL expansion to minimize representation error, as described above, is valuable, it may not be the optimal approach. In that regard, the fact that this expansion allows the most accurate representation or reconstruction of the mapped data to be achieved does not mean that it is also always the most useful expansion for classifying cardiac anomalies. For example, a different expansion could be selected that might increase the representation error but would allow a particular cardiac anomaly of interest to be more readily classified.

In that regard, one modification of the expansion that may be particularly suitable for use in this application is that described by Fukunaga et al. in an article entitled "Application of K-L Expansion to Feature Selection and Ordering: A Criterion and an Algorithm for Grouping Data," appearing in Volume C19 of IEEE Transactions on Computers at page 311. The disclosed approach is a modification of the conventional KL expansion involving the transformation of the covariance matrix before the eigenvectors are extracted.

The basis functions identified by this modified KL expansion are selected to enhance the differences between two pattern classes. More particularly, in the present application, they are selected to accentuate the difference between a "normal" class that does not exhibit the cardiac anomaly of interest and a "diseased" class that does exhibit the anomaly. The basis functions identified may not, however, be the best at reconstructing the mapped data itself.

As noted previously, however, in the current arrangement the conventional KL expansion is used to achieve the best representation of the mapped data. This approach allows the ECG/BSM system 10 to remain relatively adaptable because the initial emphasis on representation is believed to retain information that might be useful in discriminating various features. On the other hand, if the expansion were selected to enhance the classification of a particular anomaly, the utility of the expansion in subsequently classifying other anomalies could be compromised.

With the appropriate twelve basis functions established at block 82, the transformed integral data is then multiplied by the orthonormal basis functions at block 84 to produce twelve coefficients. The analysis next typically involves some form of statistical treatment of the coefficients. More particularly, even though significant processing has been performed to reduce the data presented for analysis, it may still be of sufficient scope and subtlety to render meaningful analysis difficult. As a result, some form of stepwise discriminant analysis, logistic regression, or cluster analysis, discussed generally in Afifi et al., Computer-Aided Multivariate Analysis, parts II and III, may be performed.

In that regard, the subsequent statistical analysis of the twelve coefficients is based upon information obtained from "normal" and "diseased" patient populations in a clinical setting. This information is stored in the data storage system 34 for use by the ECG/BSM system 10.

Figure 8:
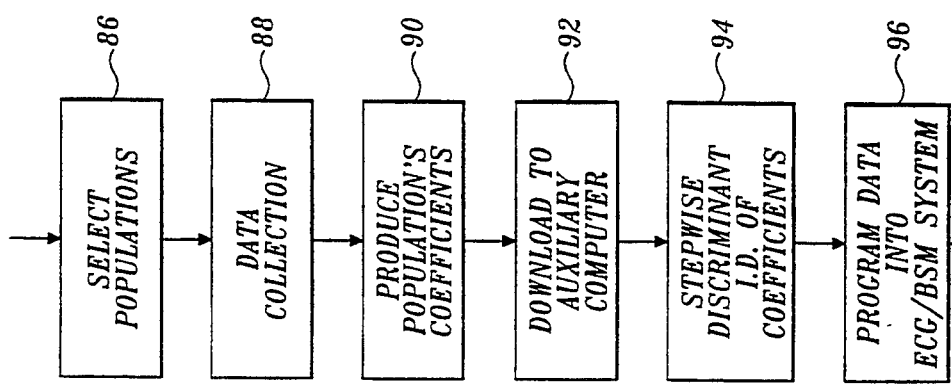
FIG. 8 is a flow chart illustrating one way in which clinical data is obtained from a patient population, including "normal" individuals, as well "diseased" individuals exhibiting the particular cardiac anomaly of interest.

Reviewing the manner in which this information is obtained in greater detail, reference is had to FIG. 8 in which the various steps to be performed are illustrated in flow chart form. First, suitable normal and diseased populations are selected as indicated at block 86.

The normal population includes a statistically adequate number of patients that are in good health, have had no history of heart disease, and have been evaluated for the absence of a particular cardiac anomaly or anomalies of interest by a generally accepted clinical technique or techniques. The diseased population, on the other hand, includes a statistically adequate number of patients that have been identified as exhibiting the particular anomaly or anomalies of interest. Where appropriate, a quantification of the clinically evaluated anomaly exhibited by each patient in the diseased population is also determined.

With suitable populations identified, data representing the electrical activity of each patient's heart is collected at block 88. In that regard, the same electrode configuration is employed and the signals sensed at the electrodes are collected in the same manner as those that will eventually be evaluated by the ECG/BSM system 10. Similarly, at block 90, the signals are processed in the manner described above in connection with blocks 52 through 84.

Thus, the collection and processing of data from the normal and diseased populations represented by blocks 88 and 90 can be performed by a prototype ECG/BSM system 10. For the arrangement described above, the data collected from each patient in the normal and diseased populations will be reduced to a set of twelve coefficients.

Next, the twelve coefficients associated with each of the patients in both populations, as well as any pertinent clinical data concerning the patients, are downloaded from the data storage system 34 of the prototype ECG/BSM system 10 to a memory system used by a suitable auxiliary computer at block 92. The computer is programmed with, for example, the BMDP LR (logistics) or TM (linear) software packages available from Statistical Software of Los Angeles, Calif. and performs a statistical analysis of this data, as described in greater detail below, to identify the particular coefficients that are most useful in detecting the particular cardiac anomaly or anomalies of interest.

More particularly, the mainframe computer performs a stepwise regression analysis on the coefficients stored for all of the patients in the normal and diseased populations as indicated at block 94. A separate such regression analysis is performed to for each feature of interest. As an initial step in the analysis, the computer first looks for the single one of the twelve coefficients that best allows the presence or absence (and perhaps extent) of the particular anomaly of interest to be identified for all individuals in the population.

In that regard, a canonical variable V or feature value is computed for each patient in the population. The canonical variable V is used to determine the ability of the coefficient(s) selected to accurately allow diseased and normal patients to be distinguished. If the computer employs a linear analysis, the variable V is calculated as:

$$w0(c0) + w1(c1) + \ldots + wn(cn)$$

where c0 through cn are the coefficients identified by the stepwise analysis and w0 through wn are weighting factors associated with each coefficient. Note that all but one of the coefficients is set equal to zero during this initial phase of the discriminant analysis. Also, if a logistic analysis is employed, the canonical variable V is used in the logarithmic analysis:

$e^V/(1+e^V)$

As part of the analysis of the canonical variable, the computer also makes assumptions about a decision boundary that divides the normal and diseased patient populations. If the canonical variable computed for a particular member of the population and particular coefficient is greater than the decision boundary or cutpoint, then the patient is considered to exhibit the cardiac anomaly of interest. On the other hand, if the variable is less than or equal to the cutpoint, then the patient is considered normal. The number of incorrect diagnoses made by this process during the evaluation of the population is then counted to estimate the probability of mistake for the particular combination of cutpoint and coefficient selected.

Ultimately, the computer identifies the single coefficient c0 that will minimize the likelihood of incorrectly distinguishing diseased and normal patients in the clinical population for all possible cutpoints. As part of the stepwise nature of the analysis, the computer next determines whether the predictive ability of the analysis can be enhanced by including another one of the coefficients in the computation of the canonical variable V. If so, the "best" additional coefficient is selected as a second coefficient to be used by system 10. This process is repeated until no additional coefficients can be used to enhance the detection and analysis of the anomaly of interest. Ultimately, the mainframe computer may determine that, for example, the third, fifth, and seventh of the twelve coefficients are the best for use in evaluating the anomaly of interest.

Once the appropriate coefficients are identified by the computer, their identification is programmed into the storage system 34 of the ECG/BSM system 10 for use in analyzing the transformed patient data and providing a suitable diagnostic output to the operator. Information concerning the nature and magnitude of the anomaly associated with the coefficients is also stored. If several different anomalies are to be evaluated, the coefficients to be used in computing each of the different canonical variables (V1, V2, through Vn) are stored, along with the related information concerning the nature of the anomalies.

Figure 9:
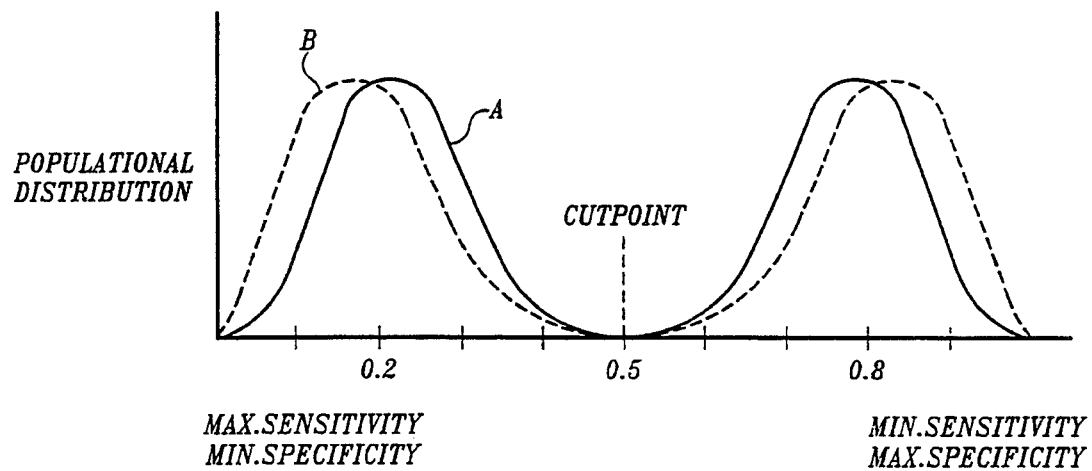
FIG. 9 is a graph depicting the distribution of the patient population relative to the sensitivity and specificity of the analysis performed.

Before leaving this discussion of the interpretation of the patient population data, the results of the populational analysis will be graphically recapped. In that regard, FIG. 9 illustrates a plot of the distribution of the canonical variables V computed for all of the patients in the normal and diseased populations using the coefficients selected by the mainframe computer as part of the stepwise regression analysis. The extreme left-hand side of the curve indicates maximum sensitivity (i.e., sensitive because all patients have a canonical variable greater than zero) and zero specificity (i.e., not specific because both normal and diseased patients are equally likely to have a variable V greater than zero). On the other hand, the extreme right-hand side of the curve indicates maximum specificity (i.e., only truly diseased patients will have a variable V equal to one) and zero sensitivity (i.e., no patients will actually have a variable equal to one).

As represented by the solid curve A in FIG. 9, the distribution of variables for a linear analysis will typically include two spaced-apart, bell-shaped sections, which generally separately represent the normal and diseased populations. By way of illustration, the variables associated with the normal population may be centered, for example, around 0.2, while the variables associated with the diseased population are centered about 0.8. A "cutpoint" can be established between these two sections of curve A at, for example, 0.5, with variables greater than 0.5 being associated with a patient exhibiting the anomaly of interest and variables less than or equal to 0.5 being associated with a normal patient. If a logistic analysis is used in place of the linear analysis, a favorable spreading of the normal and diseased sections of the curve with respect to the cutpoint may be achieved, as indicated by curve B of FIG. 9.

As will be described in greater detail below, the cutpoint may be of use to the ECG/BSM system 10 in its analysis. In that regard, the system 10 may compute the canonical variable for a given patient, using the particular ones of the patient's coefficients identified by the discriminant analysis. A threshold corresponding to the cutpoint can then be used to interpret whether the canonical variable V indicates the presence of the particular anomaly of interest. Patients having a variable V greater than the threshold can be diagnosed as suffering from the anomaly of interest, while the remaining patients are diagnosed as normal.

By adjusting the cutpoint and threshold to, for example, 0.3 the sensitivity of the analysis can be increased. This modification might be appropriate when the ECG/BSM system 10 is used as an initial screening tool to identify potentially diseased patients for futher testing because the operator would likely want to reduce the possibility of a diseased patient being diagnosed as normal. On the other hand, if the ECG/BSM system 10 is being used to identify patients needing surgery, the cutpoint and threshold used might be adjusted upward to, for example, 0.8 to increase the specificity of the analysis. Thus, the possibility of a normal patient being subjected to surgery would be reduced.

Figure 10:
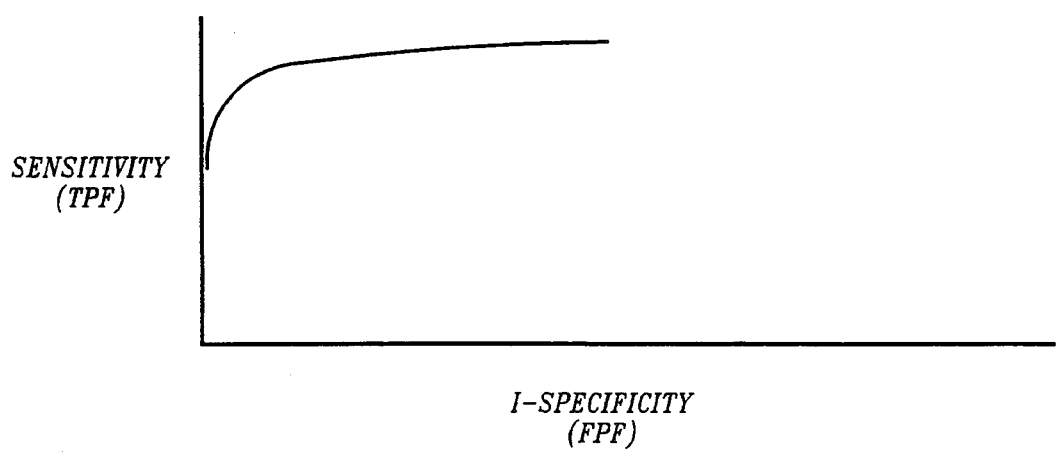
FIG. 10 is a graph of a receiver operating curve, providing an alternative depiction of the specificity/sensitivity trade-off of FIG. 9.

An alternative way of depicting the tradeoff between sensitivity and specificity inherent in the analysis is illustrated in FIG. 10. In that regard, FIG. 10 illustrates a receiver operating curve (ROC). The ROC is a plot of the data from FIG. 9, with the y-axis representing sensitivity, or true positive fraction, and the x-axis representing the quantity of "1-specificity," or false positive fraction, both expressed as percentages.

The area under the ROC curve of FIG. 10 is representative of the performance of the ECG/BSM system 10 with respect to the identification of the particular anomaly of interest. In that regard, if the particular coefficients used by the ECG/BSM system 10 could allow the system 10 to correctly diagnose all patients, the analysis would have a specificity of one and a sensitivity of one. The area under the curve of FIG. 10 would then be equal to one. Thus, the area under the curve generated for a real system will be some fraction of one.

Returning now to the detailed discussion of the analysis of an individual patient by the ECG/BSM system 10, as will be recalled from block 84 of FIG. 7, the system 10 computes twelve coefficients associated with the electrical activity of the patient's heart. An indication of the particular ones of these coefficients (e.g., the third, fifth, and seventh) to be used in the analysis of an anomaly of interest has been stored in the data storage system 34 of system 10 at block 96 of FIG. 8. In addition, information concerning various cutpoints suitable for use by system 10 in different applications has been stored, along with information concerning the nature and extent of anomalies associated with the various canonical variables to be computed.

Figure 11:
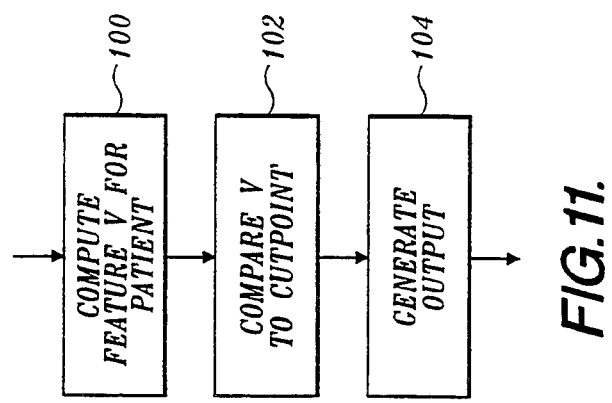
FIG. 11 is a flow chart illustrating the manner in which the system of FIG. 1 uses the information obtained in the analysis of FIG. 8 to evaluate the data transformed and compressed in accordance with FIGS. 3 and 7.

Referring now to the flow chart of FIG. 11, the ECG/BSM system 10 uses the stored information to determine the canonical variable V1 associated with the anomaly of interest at block 100. In that regard, if the analysis performed by the auxiliary computer in FIG. 8 indicated that the third, fifth, and seventh coefficients allow the anomaly to be detected with the lowest likelihood of error, then the ECG/BSM system 10 computes the variable V1 using the third, fifth, and seventh coefficients developed from the patient's data. Specifically, those coefficients are substituted into the appropriate linear or logarithmic formula for the canonical variable V.

At block 102, the canonical variable V1 is then compared against an appropriate cutpoint, which may be input by the operator either manually or as part of a mode selection process. If the cutpoint is exceeded, the patient is deemed to exhibit the anomaly of interest. On the other hand if the variable is less than or equal to the cutpoint, then the patient is considered normal.

As will be appreciated, the statistical analysis performed by the auxiliary computer included a consideration of the cutpoints to be used and their influence on the performance of the analysis. Thus, a table listing the success of the coefficients selected at correctly identifying the anomaly for the full range of cutpoints selectable can be provided to data storage 34 for use in the analysis. In that regard, the CPU 32 might be instructed to limit the range of cutpoints selectable to those that will ensure a certain predictive accuracy for the coefficients being used.

As a more sophisticated enhancement, storage 34 might be provided with multiple sets of coefficients that provide the best predictive ability for different cutpoints. The CPU 32 can then be programmed to review the cutpoint selected and decide whether an alternative set of coefficients could be to used to achieve a greater accuracy.

As will be appreciated, the resultant NORMAL versus DISEASED diagnosis can be displayed by the output system 38 of the ECG/BSM system 10 at block 104 of FIG. 11. In addition, display of the numeric value of the canonical variable V1 and the cutpoint can be provided to enhance the operator's understanding of the evaluation performed. Further insight into the analysis performed may also be achieved by plotting the patient's variable V1 on a display of the curve of FIG. 9 or 10.

The ECG/BSM system 10 can also be programmed to combine different groups of the patient's coefficients to compute different canonical variables, such as V2 and V3, associated with different anomalies of interest in the same patient. The output system 38 would then include suitable displays of each evaluation.

In addition to the basic analysis described above, clinical experience suggests that the assessment of the canonical variable V made by the ECG/BSM system 10 can be further enhanced by the inclusion of certain clinical factors that are not present in the electrical signals sensed at the electrode sites. For example, if the analysis of a patient's cardiac activity in the foregoing manner indicates a low probability of ischemia but the patient is experiencing chest pain, there is perhaps a greater likelihood of the probability being inaccurate than if no chest pain is experienced. The same is true for a patient having a personal history of myocardial infarction or a family history of cardiac disease.

The ECG/BSM system 10 can be programmed to account for these clinical factors, as well as others such as sex, age, and cholesterol levels. Specifically, an additional term corresponding to each clinical factor to be considered may be added to the computation of the canonical variable V. Alternatively, the threshold level against which the variable V is compared for diagnostic purposes may be adjusted as a function of the clinical factors present. It is expected that the inclusion of these clinical factors may result in an adjustment of up to 30 percent in the variable or cutpoint used.

The basic analysis described above for extracting features from the mapped data can be altered in various ways. One important variation involves the elimination of the transformation step. In that regard, it is possible to obtain a suitable spatial distribution of charge relying simply upon the twelve lead data collected. As will be appreciated, this simply requires a modification of the post-transformation processing in accordance with the general principles outlined above.

The inclusion of software to transform the twelve-lead data to 192-lead data does, however, offer an advantage. Specifically, alternative electrode sets including more or less than the ten electrodes discussed above can be used and the transformation process will cause the data to be converted to a form that is compatible with the existing post-transformation processing software. On the other hand, if no transformation were performed, alternative processing would be required to allow the ECG/BSM system 10 to be used with electrode sets having more or less than the ten electrodes.

Another important variation in the analysis performed by the ECG/BSM system 10 relates to the amount, or form, of the electrical activity sensed at the electrodes. In that regard, although the analysis described above is based upon the evaluation of QRST integrals, as will be appreciated, various other formats can be analyzed depending, in part, upon the nature of the cardiac anomalies of interest. For example, in addition to the QRST interval, the QRS and ST intervals can be analyzed. Also, the data collected during these intervals can be analyzed on a point-by-point basis or as a single integral representative of the entire interval.

As noted above, one determinant for the format of the signals to be analyzed is the type of cardiac characteristic to be evaluated. In that regard, as was previously described, the features of the electrical waveform sensed at any given electrode are directly related to the physiological activity of the heart. Thus, it is reasonable to expect that the particular segment of the waveform to be analyzed, as well as the way in which the segment is represented, would involve the identification of the portion of the waveform that is physiologically most closely related to the particular anomaly of interest.

As one illustration of the relationship between the waveform and the activity to be analyzed, many forms of the cardiac disease to be analyzed can be grouped as either activation-related diseases or recovery-related diseases. Activation-related diseases include, for example, necrosis, accessory pathway blockages, and bundle blockages. Recovery-related diseases, on the other hand, include ischemia and nerve disorders. Generally, activation-related diseases are considered to have the greatest impact upon the QRS segment of cardiac waveforms, while the ST segment is generally considered to be most representative of recovery-related diseases. Because the processes of activation and recovery are related, the entire QRST interval is sometimes also considered to be representative of recovery-related features, especially those involving the disparity of ventricular recovery properties.

The analysis of the integral or area of the QRST interval is reviewed above. If the data is not compressed by integration, the analysis can still proceed in much much the same manner. For example, instead of producing a single isointegral map, the ECG/BSM system 10 may generate a plurality of isopotential maps corresponding to each of the discrete segments of the interval. Basis functions may also be identified for for each discrete segment of the interval and analyzed through the use of a similar statistically constructed software package stored in the memory 34 of ECG/BSM system 10.

If, for example, each 250 to 400 segments of the QRST interval are analyzed individually, rather than as a single integral, the complexity of the processing performed by the ECG/BSM system 10, as well as the statistical analysis required to program system 10, increases by an order of magnitude. However, the advantage of this approach over the use of integrals is that the analysis is now able to account for temporally specific information in the waveform.

The analysis of the QRS interval parallels the analysis of the QRST interval, described above and may be accomplished in several different ways. For example, the map of the QRS integral, or the maps of the individual segments of the QRS interval, may be displayed at the output system 38 and visually analyzed by an experienced physician. As will be appreciated, the CPU 32 can be easily programmed to operate in the same manner described above, except that the T segments of the waveforms are eliminated prior to further processing and analysis. This analysis may be useful in identifying, for example, the presence of necrotic tissue, ventricular hypertrophy, and previous myocardial infarction.

As represented by block 104 of FIG. 11, ventricular activation time (VAT) maps can be generated and evaluated for the QRS interval. In that regard, the QRS portion of the waveform is most sensitive to ventricular activation. The VAT map provides a useful way of comparing the earliest and latest parts of the ventricle to activate, which may be indicative of the presence of, for example, ischemia or beat irregularities.

A VAT map is generated by using the fully expanded waveform data, prior to the performance of a basis function compression at block 78. The maximum negative derivatives of the waveforms corresponding to the various electrode sites are then computed. As will be appreciated, these derivatives represent ventricular activation. By displaying the maximum derivatives as isoderivative contours, a map of the earliest and latest portions of ventricle to activate is provided.

When the ST segments are to be evaluated, the CPU 32 must be programmed to alter the portions of the waveforms used in the analysis. The processing of the ST segment integral or waveform data then proceeds in the manner described above for the QRST and QRS intervals. One feature of particular interest that may be suitably identified by ST segment analysis is the detection of cardiac injury currents. In that regard, it has been found that, for example, disease-related injury or trauma to cardiac tissue may introduce a displacement or shift in the ST segment. This shift is most readily observed by a comparison of the plots of isopotential contour maps, which will readily illustrate temporal variations in the activity of the heart.

One other approach used to evaluate the ST segments involves the use of snapshots of isopotential frames. As will be appreciated, this technique requires the CPU 32 to retain the waveform data from the various electrodes collected over the cardiac cycle, before compression by the computation of integrals. Isopotential maps are then generated at block 78 in FIG. 3 for certain predetermined times during the ST segment of the cardiac cycle, such as 40, 60, or 80 milliseconds after the initiation of the interval. As will be appreciated, these snapshots can be used to evaluate injury-related ST segment displacements, as described above.

Turning now to several specific applications of interest, one cardiac anomaly that has been found to be particularly suitable for detection, using 12-lead transformed BSM data and the feature extraction techniques described above, is coronary artery stenosis. As will be appreciated, the stenosis to be detected may range anywhere from a minor reduction in an artery's diameter to a complete blockage or occlusion. The ECG/BSM system 10 is designed to detect the presence and magnitude of stenoses, as well as the artery or arteries involved.

Stenosis is typically related to ischemia. In that regard, in the presence of stenosis, the reduction in blood flow, may eventually result in ischemia of the arteriole and cardiac tissue. The ECG/BSM system 10 does not respond to the stenosis directly, but rather the effect that the attendant ischemia has on action potentials. Given the spatial sensitivity of the mapping process employed, it is possible for the system 10 to achieve the desired sensitivity.

In that regard, the 12-lead transformation and QRST area feature extraction described above have been found suitable for detecting not only the existence of stenosis, but also for discriminating between the location of the stenosis at such locations as the right coronary artery (RCA), left circumflex artery (LCX), and left anterior descending artery (LAD). By way of illustration, the performance of an ECG/BSM system 10 in this application will be briefly reviewed.

The clinically based statistical analysis used to program the system 10 to identify the appropriate coefficients for use was based upon a clinical population including 200 patients with suspected coronary artery stenosis. Coronary angiography indicated that 184 of the patients exhibited more than a 50% narrowing of at least one artery (113 LAD, 88 LCX, and 109 RCA). Out of this population of 200, 92 patients exhibited single artery stenosis or disease, 58 had double artery disease, 34 had triple vessel disease, 51 patients had experienced a previous myocardial infarction, and 16 had normal coronaries. An age-matched normal population of 137 patients was also used.

Data was collected from the population using a ECG/BSM system 10 employing ten electrodes and using the first twelve basis functions computed for the 192-lead transformation of the twelve-lead QRST integral data. The statistical package used to identify the particular coefficients suitable for evaluating the degree of stenosis in the various arteries of interest was the BMDP package identified above. As will be appreciated, this software was used to separately analyze the clinical data for each locality of stenosis.

Of the twelve resultant coefficients, the clinically based statistical analysis indicates that the first, second, fourth, and twelfth coefficients are appropriate for evaluating RCA stenosis, the first, second, third, and twelfth coefficients are appropriate for evaluating LCX stenosis, and the first, second, third, ninth, eleventh, and twelfth coefficients are appropriate for evaluating LAD stenosis. As will be appreciated, it may also be possible to identify certain coefficients that are more successful in identifying larger as opposed to smaller stenoses.

The ability of the ECG/BSM system 10 to locally detect and evaluate the different stenoses of the clinical population was then evaluated, with the following results:

| Artery | Sensitivity | Specificity | Predictive Accuracy |
|--------|-------------|-------------|---------------------|
| LAD    | 85%         | 80%         | 82%                 |
| LCX    | 78%         | 84%         | 82%                 |
| RCA    | 82%         | 82%         | 82%                 |
| CAD    | 82%         | 81%         | 81%                 |

The CAD value listed is a cumulative estimation of the existence of stenosis in any vessel, obtained, for example, not through the development of separate CAD coefficients, but rather through a combined weighting of the LCX and LAD coefficients. The advantage of this combined weighting is that it frequently allows a more accurate overall detection of stenosis to be achieved. This approach has been found effective at detecting and localizing stenoses as small as 20% to 40% of vessel diameter.

The areas of the ROC curves generated for the different localities evaluated by the system 10 are 0.871 for LAD, 0.894 for LCX, 0.866 for RCA, and 0.896 for CAD. The performance available from exercise treadmill testing (ETT) which is the currently accepted clinical standard, is a sensitivity of 66% and a specificity of 84%. Thus, the performance of the ECG/BSM system 10 represents a significant enhancement over ETT. The relative simplicity of the system 10 interfaces, its noninvasive nature, and the elimination of exercise as a test condition are among other advantages the ECG/BSM system 10 has over ETT.

One enhancement of the preceding CAD analysis involves the way in which the magnitude of stenosis can be evaluated. In that regard, thallium testing can be used to gather clinical data concerning stenosis over five different cardiac regions: lateral, inferior, apical, anterior, and septal. As will be appreciated, the best coefficients for evaluating disease in these regions can then be determined in accordance with the analysis depicted in FIG. 8.

In one arrangement, a canonical variable V is computed for each of these five regions and compared against a cutpoint as part of a normal versus diseased diagnosis for each region. The magnitude of the stenosis present in the LAD, LCX, or RCA can then be judged depending upon the number of the more limited regions in which stenosis is present. In that regard, the anterior and lateral subregions are combined in the evaluation of the magnitude of LAD stenosis. The lateral and apical regions are used in the LCX evaluation, while the inferior and septal regions are used in the RCA evaluation. With two subregions involved in the analysis of each artery, the resultant magnitude output can be simply GREATER THAN 50%, if both subregions are diseased, and LESS THAN 50%, if only one subregion is diseased.

Another cardiac characteristic that appears to be particularly suitable for analysis with 12-lead transformed BSM data is EP inducibility. Inducibility basically refers to the ability of an electrical shock, applied to the heart of a patient who has had a history of cardiac arrhythmia, such as fibrillation, to induce that arrhythmia. Drugs can be administered to the patient to reduce his or her susceptibility to the arrhythmia and a measurement of the patient's inducibility then becomes a measure of the drugs' efficacy.

The evaluation of inducibility is performed in largely the same manner as described for stenosis detection above. Of course, the population used to construct the analytical software relied upon by the system 10 differs. The coefficients selected for further evaluation are one, three, five and eight. Otherwise, the twelve-lead transformation of QRST area data may still be used and processed as described previously.

Another particularly suitable application for the ECG/BSM system 10 involves the distinguishing of reversibly ischemic tissue from necrotic or dead tissue. In that regard, conventional evaluations involve the injection of thallium into a patient's blood stream. The patient's body is then imaged immediately after injection using gamma radiation, as well as some interval of time later. Healthy tissue will be immediately perfused and, as a result, exhibit thallium presence in the initial image. Reversibly ischemic tissue will not have thallium present in the initial image, but some perfusion will occur prior to the later imaging. Necrotic tissue will exhibit no perfusion either time.

Unfortunately, the images generated are extremely difficult to evaluate by all but the most experienced practitioners. Further, the invasive nature of the thallium injection and gamma radiation limits the desirability of the evaluation and the equipment is extremely expensive and not widely available. By constructing the ECG/BSM system 10 to collect cardiac data and select and evaluate coefficients based upon a thallium-based clinical population, however, a noninvasive diagnosis can be quickly and simply made.

The design of system 10 parallels that described above. Because the thallium testing offers relatively detailed regional information, however, the regional sensitivity or localizing ability of the system 10 can be enhanced. As discussed above in connection with the evaluation of stenosis, additional regional information may offer some insight into the quantification of disease.

Although not discussed in detail, the ECG/BSM system 10 could also be used to evaluate other cardiac anomalies. For example, the system 10 might be used to evaluate the risk of arrythmia due to abnormal distribution of recovery properties. Similarly, the system 10 might be used to evaluate reperfusion or restenosis after thrombolytic therapy of percutaneous angioplasty.

As will be appreciated, the operation of system 10 can be varied in a multitude of ways. For example, the data collected initially can be selected with the use of alternative waveform templates and tolerances to allow cardiac cycles containing spurious features of interest to be evaluated. Similarly, the data collected can be reviewed over a number of cardiac cycles and a given signal averaged during any interval or specific time during the processing or the various signals averaged together. In addition, as suggested, above, the portion of the waveform that is analyzed over each cycle can be altered as desired. Further, the manner in which the data may be compressed, expanded, and statistically interpreted can vary, along with the cardiac features to be detected and analyzed.

Regardless of its form, the ECG/BSM system 10 offers a number of advantages over existing systems. In that regard, most currently accepted evaluation tools involve an invasive examination that may significantly limit the ability or desirability of routinely examining larger populations to diagnose cardiac conditions at an early time, when they are often most readily treated.

Further, in comparison to existing electrocardiographic systems, the system 10 advantageously offers the spatial sensitivity available only with the emerging BSM systems including a substantially larger array of electrodes. As a result, the system again has a more widespread applicability. Further, the feature extraction techniques employed can be used with any mapping-type electrode layout to produce an enhanced evaluation of the electrical activity of the patient's heart.

Those skilled in the art will recognize that the embodiments disclosed herein are exemplary in nature and that various changes can be made therein without departing from the scope and the spirit of the invention. In that regard, and as was previously mentioned, the hardware of the system may be included in a single device or as a plurality of discrete components or systems. Further, it will be recognized that although nine leads of data are described in connection with the transformation process disclosed, the advantages of the invention can be achieved with some variation of the number of leads employed, below the number previously deemed suitable. Because of the above and numerous other variations and modifications that will occur to those skilled in the art, the following claims should be limited to the embodiments illustrated and disclosed herein.

The embodiments of the invention in which an exclusive property or privilege is claimed are defined as follows:

1. A system for determining the probability of a patient having a coronary disease, comprising:
    a first set of electrodes for receiving a first set of cardiac signals from a patient;
    computing means coupled to the first set of electrodes for transforming the first set of cardiac signals into a second set of cardiac signals such that the first set of cardiac signals appear as if they had been received from a reference set of electrodes;
    means for storing a probability function that relates three or more statistically determined coefficients taken from a set of coefficients to the probability that a patient has a coronary disease;
    means for multiplying the second set of cardiac signals by a predetermined set of basis functions to produce the three or more statistically determined coefficients; and
    means for calculating the probability function with the values of the three or more statistically determined coefficients to calculate the probability of the patient having the coronary disease.

2. The system of claim 1, wherein the first set of electrodes comprises a four-electrode limb set and a six-electrode precordial set.

3. The system of claim 1, wherein the reference set of electrodes comprises a set of 192 body surface mapping electrodes.

4. The system of claim 1, wherein the first set of cardiac signals obtained from a patient comprise integrals of a patient's QRST waveform.

5. The system of claim 1, wherein the second set of cardiac signals is represented as a vector, the system further comprising:
    means for normalizing the vector to reduce the influence of non-cardiac factors on the magnitude of the vector by scaling the vector to a unit length.

6. The system of claim 1, wherein the basis functions are identified using a Karhunen-Loeve (KL) expansion.

7. The system of claim 1, wherein the probability function that relates the three or more statistically determined coefficients taken from the set of coefficients is derived by calculating sets of coefficients for a group of patients having the coronary disease and sets of coefficients of a group of patients not having the coronary disease, and performing a statistical analysis on the sets of coefficients obtained from both groups to select which three or more coefficients from the sets of coefficients best predict the presence of the coronary disease and the probability function that relates the three or more selected coefficients to the probability that a patient has a coronary disease.

8. The system of claim 7, wherein the statistical analysis used is a linear analysis.

9. The system of claim 7, wherein the statistical analysis used is a logarithmic analysis.

10. The system of claim 1, further comprising:
    means for storing a cutpoint value above which the probability function indicates that the patient has the cardiac disease and below which the probability function indicates the patient does not have the disease;
    means for comparing the result of the probability function that is computed using the values of the three or more statistically determined coefficients to the cutpoint; and
    display means for indicating whether the patient has the coronary disease or not.

11. The system of claim 1, wherein the coronary disease is stenosis of the right coronary artery, left circumflex artery, and left anterior descending artery; necrosis, accessory pathway blockages, bundle blockages, ischema, and cardiac nerve disorders.

12. The system of claim 1, wherein the basis functions are the eigenvectors of the covariance matrix of the second set of cardiac signals and the three or more statistically determined coefficients used in the probability function are selected from the first twelve coefficients obtained by multiplying the second set of cardiac signals by the basis functions.

13. A method for determining the probability of a patient having a coronary disease, comprising the steps of:
    receiving a first set of cardiac signals from a first set of electrodes that are coupled to a patient;
    transforming the first set of cardiac signals into a second set of cardiac signals such that the first set of cardiac signals appear as if they had been received from a reference set of electrodes;
    storing a probability function that relates three or more statistically determined coefficients taken from a set of coefficients to the probability that a patient has a coronary disease;
    multiplying the second set of cardiac signals by a predetermined set of basis functions to produce the three or more statistically determined coefficients; and
    calculating the probability function with the values of the three or more statistically determined coefficients to calculate the probability of the patient having the coronary disease.

14. The method of claim 13, wherein the first set of electrodes comprises a four-electrode limb set and a six-electrode precordial set.

15. The method of claim 13, wherein the reference set of electrodes comprises a set of 192 body surface mapping electrodes.

16. The method of claim 13, wherein the first set of cardiac signals obtained from a patient comprise integrals of a patient's QRST waveform.

17. The method of claim 13, wherein the second set of cardiac signals is represented as a vector, the method further comprising the step of:

normalizing the vector to reduce the influence of non-cardiac factors on the magnitude of the vector by scaling the vector to a unit length.

18. The method of claim 13, wherein the basis functions are identified using a Karhunen-Loeve (KL) expansion.

19. The method of claim 13, wherein the probability function that relates the three or more statistically determined coefficients taken from the set of coefficients is derived by calculating sets of coefficients for a group of patients having the coronary disease and sets of coefficients of a group of patients not having the coronary disease, and performing a statistical analysis on the sets of coefficients obtained from both groups to select which three or more coefficients from the sets of coefficients best predict the presence of the coronary disease and the probability function that relates the three or more selected coefficients to the probability that a patient has a coronary disease.

20. The method of claim 19, wherein the statistical analysis used is a linear analysis.

21. The method of claim 19, wherein the statistical analysis used is a logarithmic analysis.

22. The method of claim 19, further comprising the steps of:

storing a cutpoint value above which the probability function indicates that the patient has the cardiac disease and below which the probability function indicates the patient does not have the disease;

comparing the result of the probability function that is computed using the values of the three or more statistically determined coefficients to the cutpoint; and displaying and indication of whether the patient has the coronary disease or not.

23. The method of claim 13, wherein the coronary disease is stenosis of the right coronary artery, left circumflex artery, and left anterior descending artery, necrosis, accessory pathway blockages, bundle blockages, ischema, and cardiac nerve disorders.

24. The method of claim 13, wherein the basis functions are the eigenvectors of the covariance matrix of the second set of cardiac signals and the three or more statistically determined coefficients used in the probability function are selected from the first twelve coefficients obtained by multiplying the second set of cardiac signals by the basis functions.

* * * * *